(12) United States Patent
Mitariten

(10) Patent No.: US 8,158,378 B2
(45) Date of Patent: Apr. 17, 2012

(54) UTILIZING WASTE TAIL GAS FROM A SEPARATION UNIT BIOGAS UPGRADE SYSTEMS AS BENEFICIAL FUEL

(75) Inventor: Michael Mitariten, Pittstown, NJ (US)

(73) Assignee: Guild Associates, Inc., Dublin, OH (US)

( * ) Notice: Subject to any disclaimer, the term of this patent is extended or adjusted under 35 U.S.C. 154(b) by 204 days.

(21) Appl. No.: 12/699,395

(22) Filed: Feb. 3, 2010

(65) Prior Publication Data

US 2011/0189746 A1    Aug. 4, 2011

(51) Int. Cl.
- *C12Q 1/02* (2006.01)
- *C12P 21/06* (2006.01)
- *C12P 5/02* (2006.01)
- *C12N 15/00* (2006.01)

(52) U.S. Cl. ....... 435/29; 435/69.1; 435/320.1; 435/167

(58) Field of Classification Search .............. 435/29, 435/69.1, 320.1, 167
See application file for complete search history.

(56) References Cited

U.S. PATENT DOCUMENTS

| | | |
|---|---|---|
| 3,430,418 A | 3/1969 | Wagner |
| 3,751,878 A | 8/1973 | Collins |
| 3,986,849 A | 10/1976 | Fuderer et al. |
| 4,067,801 A | 1/1978 | Ishida et al. |
| 4,077,779 A | 3/1978 | Sircar et al. |
| 4,157,958 A | 6/1979 | Chow |
| 4,372,856 A | 2/1983 | Morrison |
| 4,503,154 A | 3/1985 | Paton |
| 4,529,513 A | 7/1985 | McLennan |
| 4,676,906 A | 6/1987 | Crawford et al. |
| 4,733,528 A | 3/1988 | Pinto |
| 4,735,724 A | 4/1988 | Chynoweth et al. |
| 4,863,492 A * | 9/1989 | Doshi et al. ............ 95/8 |
| 5,015,384 A | 5/1991 | Burke |
| 5,053,058 A | 10/1991 | Mitariten |
| 5,143,835 A | 9/1992 | Nakatsugawa et al. |
| 5,411,721 A | 5/1995 | Doshi et al. |
| 5,464,766 A | 11/1995 | Bruno |
| 5,525,229 A | 6/1996 | Shih |
| 5,567,325 A | 10/1996 | Townsley et al. |
| 5,626,755 A | 5/1997 | Keyser et al. |
| 5,709,796 A | 1/1998 | Fuqua et al. |
| 5,746,919 A | 5/1998 | Dague et al. |
| 5,821,111 A | 10/1998 | Grady et al. |
| 5,863,434 A | 1/1999 | Masse et al. |
| 5,906,931 A | 5/1999 | Nilsson et al. |
| 6,248,794 B1 | 6/2001 | Gieskes |
| 6,299,774 B1 | 10/2001 | Ainsworth et al. |
| 6,824,682 B2 | 11/2004 | Branson |
| 7,033,822 B2 | 4/2006 | Maston |
| 7,481,940 B2 | 1/2009 | Clifford, III et al. |
| 2003/0111410 A1 | 6/2003 | Branson |
| 2007/0212286 A1 | 9/2007 | Shah et al. |
| 2008/0282612 A1 | 11/2008 | De Bas et al. |
| 2008/0302722 A1 | 12/2008 | Burke |
| 2010/0298450 A1 * | 11/2010 | Datta et al. ............ 518/702 |

* cited by examiner

*Primary Examiner* — Karen Carlson
*Assistant Examiner* — Natalie Moss
(74) *Attorney, Agent, or Firm* — Frenkel & Associates, PC

(57) ABSTRACT

The invention relates to a method for utilizing low-quality tail gas derived from a pressure swing adsorption system or membrane system, which is used to upgrade biogas, as a beneficial fuel for the facility and/or digester boiler.

15 Claims, 2 Drawing Sheets

UTILIZING WASTE TAIL GAS FROM A SEPARATION UNIT BIOGAS UPGRADE SYSTEMS AS BENEFICIAL FUEL

FIELD OF THE INVENTION

This invention relates to an improved process for anaerobic digestion. In particular, this invention relates to improving the process efficiency of the anaerobic digestion process.

BACKGROUND OF THE INVENTION

The safe disposal of waste or contaminating materials has been recognized as a significant health and economic issue for many years. The ability to merely dump raw materials into the oceans or landfills is no longer an acceptable mechanism for disposal of the waste. Waste organic matter including that found in raw wastewater (i.e., sewage), sludge from sewage treatment facilities, farm waste, organic industrial waste, leachate, and so forth is a principle cause of water pollution. Therefore, waste organic matter from these and other sources ideally is treated before release into the environment in order to reduce or eliminate the presence of environmentally harmful organic compounds.

One method of treating waste organic matter, especially in wastewater treatment plants and concentrated animal farms, is through anaerobic digestion. Anaerobic digestion is the biological degradation of organic material without oxygen present in which bacteria degrade or digest or decompose the organic matter fed into the system. The anaerobic digestion process has been utilized to treat and remove organic compounds from waste products such as sewage, sewage sludge, chemical wastes, food processing wastes, agricultural residues, animal wastes, including manure and other organic waste and material. As is well known, organic waste materials are fed into an anaerobic digestion reactor or tank which is sealed to prevent entrance of oxygen and in these airfree or "anoxic" conditions, anaerobic bacteria digests the waste. Anaerobic digestion may be carried out in a single reactor or in multiple reactors of the two-stage or two-phase configuration. Heat is normally added to the reactor or reactors to maintain adequate temperatures for thermophilic or mesophilic bacteria which accomplish the breakdown of the organic material. Mixing of the wastes by either mechanical or gas recirculation is can be provided to accelerate digestion.

The products or effluent from anaerobic digestion consist of: (1) a gas phase containing methane, carbon dioxide, and trace amounts of other gases, such as hydrogen sulfide, which in total comprise what is commonly called biogas; (2) a liquid phase containing water, dissolved ammonia nitrogen, nutrients, organic and inorganic chemicals; and (3) a colloidal or suspended solids phase containing undigested organic and inorganic compounds, and synthesized biomass or bacterial cells within the effluent liquid. The gas phase (biogas), if captured, can be utilized as a valuable clean fuel for heat and power generation or transportation. By capturing the biogas, the use of anaerobic digestion can produce valuable energy from waste streams of natural materials or to lower the pollution potential of a waste stream.

The biogas generated from anaerobic digesters in wastewater treatment plants (WWTPs) and concentrated animal farms usually comprises a mixture of several gases and vapors, mainly methane and carbon dioxide. This biogas is rich in methane, typically containing 50-70% methane with the balance being carbon dioxide, hydrogen sulfide, water, and siloxanes. The methane in the biogas contains the bulk of the energy value of the biogas, and thus, this methane in the biogas allows the biogas to be burned for heat or used to fuel an electric generator among other uses. Most WWTPs and farms use a portion of this gas to provide fuel to their digester and process boiler. Unfortunately, using the biogas as a fuel for the digester and process boiler can consume over 50% of the total gas generated.

In many cases, the portion of the biogas not used as fuel for the digester and/or process boiler is flared. Flaring the gas ejects millions of BTUs to the atmosphere that might otherwise be put to good use. In addition to wasting the BTUs that this portion of biogas could provide, flaring of the excess biogas also results in release of significant quantities of so-called "greenhouse gases" such as carbon dioxide. The atmospheric levels of greenhouse gases, which include carbon dioxide ($CO_2$) are rising rapidly and are believed to be a significant factor in the rise in global warming and its potential impact on the earth's climate, ocean levels and human lifestyles. Carbon dioxide levels in the earth's atmosphere are at historic high levels. Although the greenhouse warming potential of carbon dioxide is small compared to some of the other greenhouse gases, due to the sheer mass of carbon dioxide emitted into the atmosphere, carbon dioxide presently has a significant impact as a greenhouse gas in the atmosphere.

It is estimated that globally, over 24 billion metric tons of carbon dioxide were emitted into the earth's atmosphere in 2001 as a result of burning fossil fuels. Some predict that by the year 2025, global emissions of carbon dioxide may reach 35 billion tons. If it is possible to capture and use a significant amount of the biogas that would otherwise be flared and released as greenhouse gases into the atmosphere, the potential impact of carbon dioxide on global warming may be limited. Thus, in addition to the economic waste caused by flaring the excess biogas that could otherwise be used as fuel, flaring has become an unacceptable disposal method of the biogas because flaring the biogas wastes a diminishing hydrocarbon resource and is also a source of air pollution.

In an attempt to be more energy efficient and utilize a portion of the biogas obtained from anaerobic digestion, many WWTPs have installed on-site electric generators to make use of the digester gas energy. If the gas composition of the biogas contains a minimum amount of methane required to provide adequate energy upon combustion, a fuel stream is fed from the biogas stream to an engine driving an electrical generator capable of being powered by the combustion of the methane. The electrical generator is provided to generate a minimum amount of electricity to provide power to the facility and any excess can be exported from the facility. Electrical generation, however, is costly and maintenance is intensive and, in most regions of the country, does not provide the WWTP facility with any savings over purchased electricity. In fact, the high maintenance and operating costs involved in using an electrical generator have compelled many wastewater treatment plants to abandon the use of electric generators, and return to flaring the gas. The recent focus on self-sustainability, energy conservation, and the need to reduce greenhouse gases has prompted these plants to seek new alternatives for utilizing the energy in the flared gas.

One alternative to the use of electric generators for utilizing a portion of biogas not used as fuel is using a pressure swing adsorption (PSA) system to upgrade the biogas to pipeline quality which would provide a clean gas for on-site use, for sales to the pipeline, or for compressed natural gas. Pressure swing adsorption (PSA) technology has recently found application for upgrading the biogas from anaerobic digesters to produce a valuable high-BTU fuel that can be sold directly to the pipeline or converted to compressed natural gas (CNG) or liquid natural gas (LNG).

Pressure swing adsorption is a well-known method for the separation of bulk gas mixtures and for the purification of gas streams containing undesirable impurities. Gas separations by pressure swing adsorption (PSA) are achieved by coordinated pressure cycling of a bed of adsorbent material which preferentially adsorbs at least one or more readily adsorbable components present in a feed gas mixture relative to at least one less readily adsorbable component present in the feed gas mixture. That is, the bed of adsorbent material is contacted with a ready supply of a feed gas mixture. During intervals while the bed of adsorbent material is subjected to the ready supply of feed gas mixture and the bed is at or above a given feed pressure, a supply of gas depleted in the at least one more readily adsorbable component may be withdrawn from the bed. Eventually, the adsorbent material in the bed becomes saturated with the at least one more readily adsorbable component and must be regenerated. At which point, the bed is isolated from the ready supply of feed gas mixture and a gas enriched in the at least one more readily adsorbable component is withdrawn from the bed, regenerating the adsorbent material. In some instances, the bed may be subjected to a purge with depleted gas to facilitate the regeneration process. Once the adsorbent material is sufficiently regenerated, the bed is again subjected to the ready supply of feed gas mixture and depleted gas can once again be withdrawn from the bed once the pressure on the bed is at or above the given feed pressure. This cycle may be performed repeatedly as required.

The adsorbent material selected for use in the pressure swing adsorption units depends on the component to be separated from the feed stream. Adsorbent materials suitable for use in the pressure swing adsorption apparatus include, but are by no means limited to, activated carbon; carbon molecular sieve (CMS) adsorbents; activated alumina; silica gels; zeolites; and the titanium silicates. One skilled in the art is able to select a given adsorbent material or mixtures thereof, for use with a given feed gas mixture and desired product materials.

Numerous patents describe PSA processes for separating carbon dioxide from methane or other gases. One of the earlier patents in this area is U.S. Pat. No. 3,751,878, which describes a PSA system using a zeolite molecular sieve that selectively adsorbs $CO_2$ from a low quality natural gas stream operating at a pressure of 1000 psia, and a temperature of 300° F. The system uses carbon dioxide as a purge to remove some adsorbed methane from the zeolite and to purge methane from the void space in the column. U.S. Pat. No. 4,077,779, describes the use of a carbon molecular sieve that adsorbs $CO_2$ selectively over hydrogen or methane. After the adsorption step, a high pressure purge with $CO_2$ is followed by pressure reduction and desorption of $CO_2$ followed by a rinse at an intermediate pressure with an extraneous gas such as air. The column is then subjected to vacuum to remove the extraneous gas and any remaining $CO_2$.

The use of PSA technology for upgrading digester biogas is relatively new and only a few PSA systems have been installed on digesters. PSA, and other purification methods such as membranes, separate the compounds in the biogas into two streams, one rich in methane (referred to as the product) and the other rich in contaminants (referred to as the tail gas). Irrespective of how efficient the separation process is, the PSA tail gas still contains some methane, on the order of 11 to 20%. The low methane level of the tail gas and the presence of contaminants, such as siloxanes, render the tail gas unusable as an engine fuel to drive pumps, blowers, or generators. To date, the tail gas has been disposed in a thermal oxidizer or flare. These disposal systems for the tail gas can be expensive especially on gases below 200 BTU/cf and can require supplemental high-purity gas. This minimum requirement on the BTUs of the gases required by the disposal systems compromises the economic viability of a gas upgrade project. Most likely due to the recent emergence of gas separation systems for upgrading digester gas, to date, there is no evidence to indicate that any strategies have been advanced to address this problem.

The low-BTU tail gas stream produced by the PSA system is too low in heating value to be directly useful as a fuel and requires disposal in a flare or thermal oxidizer. The low-BTU tail gas stream consists largely of carbon dioxide, moisture, hydrogen sulfide, other contaminants, and low levels of methane. The composition of the tail gas stream does not contain a sufficient methane concentration to provide adequate energy upon combustion. While this tail gas is too low in heating value to be useful as a fuel, the amount of tail gas is significantly large in volume and therefore represents a considerable loss of valuable methane. Moreover, flares are capital intensive and can be difficult to operate on very low quality fuels. Furthermore, using a PSA system still requires gas being flared, which means that PSA upgrading represents only a partial solution to the recovery of digester gas. What is needed is an environmentally and economically sound strategy for eliminating flaring and disposal of the tail gas produced by the biogas upgrading process.

SUMMARY OF THE INVENTION

This invention relates to a method for utilizing as a fuel supplement the otherwise wasted tail gas, which is derived from a separation unit, such as a pressure swing adsorption unit or a membrane unit, on the biogas produced from an anaerobic digestion unit.

DETAILED DESCRIPTION OF THE INVENTION

Figure 1:
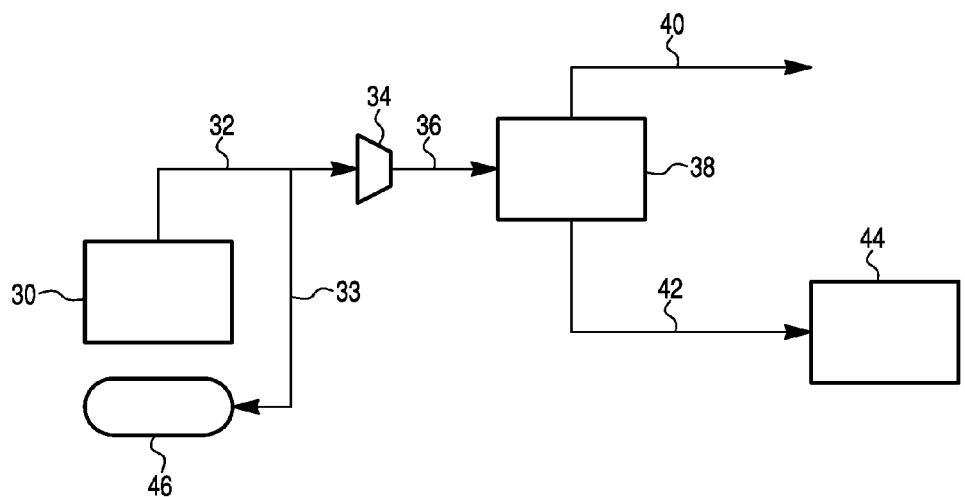
FIG. 1 is a schematic of a prior art biogas production system wherein the tail gas from the pressure swing adsorption unit is flared.

The present invention is directed to utilizing the low-quality tail gas derived from a pressure swing adsorption (PSA) system, which is used to upgrade anaerobic digester biogas, as a beneficial fuel for the facility and/or digester boiler. Additionally, the present invention is also directed to utilizing the low-quality permeate derived from a membrane separation system, which is used to upgrade anaerobic digester biogas. Traditionally, the low-quality tail gas from the PSA system does not contain a sufficient methane concentration to provide adequate energy upon combustion to be used as a fuel and is thus disposed of by flaring in a flare or a thermal oxidizer. In accordance with this invention, instead of flaring the tail gas, an intermediate-quality gas is produced by either blending the tail gas with higher quality digester gas, and the blended intermediate-quality gas functions as a fuel for boilers, or operating the PSA system or membrane system such that the tail gas or permeate produced is an intermediate-quality gas. Key to this strategy is recognizing the heat demands of the digester relative to the digester gas production (parasitic load) and PSA feed, and maintaining a satisfactory fuel blend for the boiler used to heat the digester. For those applications where the parasitic load is greater than 33%, the tail gas can be used as fuel, rather than disposed of as flared gas. Utilizing the intermediate-quality blended gas as a fuel can eliminate the need for an expensive and maintenance intensive flare and provides for complete utilization of all digester gas, which will reduce the environmental impact of the anaerobic digester. The economic and political consequences of this strategy are significant, particularly for a municipal wastewater treatment plant, where the populace is expecting government facilities to adopt self-sustaining and energy conserving technology.

In the present invention, an anaerobic digestion process is utilized to treat and remove organic compounds from waste products such as sewage, sewage sludge, chemical wastes, food processing wastes, agricultural residues, animal wastes, including manure and other organic waste and material. Organic waste materials are fed into an anaerobic digestion reactor or tank which is sealed to prevent entrance of oxygen and in these airfree or "anoxic" conditions, anaerobic bacteria digests the waste. Anaerobic digestion may be carried out in a single reactor or in multiple reactors of the two-stage or two-phase configuration. See, S. Stronach, T. Rudd & J. Lester, Anaerobic Digestion Processes in Industrial Wastewater Treatment, 1986, Springer, Verlag, pp. 93-120 for single reactors and pp. 139-147 for multi-stage operations. The products or effluent from anaerobic digestion consist of: (1) a gas phase containing methane, carbon dioxide, and trace amounts of other gases, such as hydrogen sulfide, which in total comprise what is commonly called biogas; (2) a liquid phase containing water, dissolved ammonia nitrogen, nutrients, organic and inorganic chemicals; and (3) a colloidal or suspended solids phase containing undigested organic and inorganic compounds, and synthesized biomass or bacterial cells within the effluent liquid.

Methods for the anaerobic digestion or treatment of sludge, animal waste, synthesis gas or cellulose-containing waste are disclosed in, among others, U.S. Pat. No. 5,906,931 to Nilsson et al., U.S. Pat. No. 5,863,434 to Masse et al., U.S. Pat. No. 5,821,111 to Grady et al. U.S. Pat. No. 5,746,919 to Dague et al., U.S. Pat. No. 5,709,796 to Fuqua et al., U.S. Pat. No. 5,626,755 to Keyser et al., U.S. Pat. No. 5,567,325 to Townsley et al., U.S. Pat. No. 5,525,229 to Shih, U.S. Pat. No. 5,464,766 to Bruno, U.S. Pat. No. 5,143,835 to Nakatsugawa et al., U.S. Pat. No. 4,735,724 to Chynoweth, U.S. Pat. No. 4,676,906 to Crawford et al., U.S. Pat. No. 4,529,513 to McLennan, U.S. Pat. No. 4,503,154 to Paton, U.S. Pat. No. 4,372,856 to Morrison, U.S. Pat. No. 4,157,958 to Chow, and U.S. Pat. No. 4,067,801 to Ishida et al. These patents disclose different processes and equipment for the bioconversion, either by microbial digestion or enzymatic conversion, of those materials into methane and other useful materials.

The equipment used for the anaerobic digestion of waste into a biogas, which contains methane, varies greatly and is generally tailored to specific applications, which is known by one skilled in the art. Equipment that is suitable for a first type of feedstock generally has to be modified before it can be used for a second different type of feedstock.

The anaerobic microbe used in the anaerobic digester is any anaerobic bacterium, fungus, mold or alga, or progeny thereof, which is capable of converting the feedstock to a useful material in the anaerobic digester of the invention. Anaerobic microbes can be isolated from decaying or composted feedstock, can be endogenous to the area in which the feedstock was first obtained, and can be obtained from bacterial or fungal collections such as those of the American Type Culture Collection (ATCC) or have been genetically altered or engineered to convert a feedstock to a useful material.

The conditions inside the anaerobic digester in the present invention will vary according to the useful material being produced, the anaerobic microbe being used, the configuration of the anaerobic digester, the feedstock being converted, the desired productivity of the anaerobic digester, and the form of microbe (immobilized or free-flowing) used. Immobilized microbes can be prepared using any methods known by the artisan of ordinary skills in the arts. The conditions used to culture the anaerobic microbe and maintain it viable in the anaerobic digester can be varied. Conditions which can be controlled include solids content, reaction solution composition, temperature, gas content, digestion rate, anaerobic microbe content, agitation, feed and effluent rates, gas production rate, carbon/nitrogen ratio of the feedstock, pressure, pH, and retention time in the digester, among other things.

In particular, temperature affects the productivity of the anaerobic digester. Heat is normally added to the reactor or reactors to maintain adequate temperatures for thermophilic or mesophilic bacteria which accomplish the breakdown of the organic material. Generally, elevating the temperature will increase the productivity, e.g. faster or more efficient gas production, of the digester up to a temperature that is harmful to the microbial flora in the digester, at which temperature productivity will decrease. To fuel the heating component of the anaerobic digester, the biogas produced by the digester can be used. However, as discussed earlier, the use of the biogas produced by the digester as the sole fuel is an inefficient use of the total energy contained in the biogas produced by the anaerobic digester.

Typical biogas generated from biomass of wastewater treatment plants and concentrated animal farms generate a methane-rich biogas, which typically contains 50-70% methane with the balance being carbon dioxide, hydrogen sulfide, water, and siloxanes. Most plants only use a portion of this gas to provide fuel for their digester and process boiler. This use of the biogas can consume over 50% of the total gas generated, in many cases, the portion of gas not used as a fuel is flared. Flaring the gas rejects millions of BTUs to the atmosphere that might otherwise be put to good use.

Pressure swing adsorption (PSA) technology has recently found application for upgrading the biogas generated from anaerobic digestion to a high-BTU fuel that can be sold directly to the pipeline or converted to CNG or LNG. The PSA process splits the biogas feed into two streams, a high-BTU product stream and a low-BTU tail gas stream consisting largely of carbon dioxide, moisture, hydrogen sulfide, other contaminants, and low levels of methane.

FIG. 1 illustrates a typical prior art biomass treatment system utilizing an anaerobic digester that produces biogas and a PSA system that upgrades the biogas from the anaerobic digester. In such a process, an anaerobic digester 30 produces a biogas stream 32 containing 50-70% methane with the balance being carbon dioxide, hydrogen sulfide, water, and siloxanes. Anaerobic digester 30 can be of any type known in the art including those discussed above. The biogas stream 32 is directed from anaerobic digester 30 to a compressor 34 that compresses the biogas stream 32 to the appropriate operating pressure and produces a compressed biogas stream 36. A portion of the biogas stream 32 is sometimes used to heat boiler 46 for the anaerobic digester 30. The compressed stream 36 is then sent to the PSA (and vacuum pump) unit 38. The PSA unit 38 contains a selective gas adsorbent as known in the art. The adsorbent used in PSA unit 38 is any known methane selective adsorbent. Adsorbent materials suitable for use in the PSA unit 38 include, but are by no means limited to, activated carbon; carbon molecular sieve (CMS) adsorbents; activated alumina; silica gels; zeolites; and the titanium silicates. One skilled in the art is able to select a given adsorbent material or mixtures thereof, for use with a given feed gas mixture and desired product materials. The PSA unit 38 produces a high-quality methane stream by selectively adsorbing much of the carbon dioxide, moisture, hydrogen sulfide, and other contaminants over the less readily adsorbable methane in the biogas stream. A high-quality methane output stream 40 is discharged at one end of the PSA unit 38. The PSA unit 38 also delivers a low pressure output stream 42 containing the desorbed impurities (carbon dioxide, moisture, hydrogen sulfide, and other contaminants) from the adsorption beds, which is generally referred to as "tail gas". The composition of the tail gas 42 contains much of the carbon dioxide, moisture, hydrogen sulfide, and other contaminants from the biogas feed stream 36. While the majority of methane is contained in the high-quality methane product stream 40, the PSA unit 38 also adsorbs a significant amount of the methane from the biogas feed which is then contained in tail gas 42 during the desorption of the PSA unit 38. However, because the concentration of methane in tail gas 42 is too low to provide an adequate heating value to be useful as a fuel, tail gas 42 requires disposal in a flare or thermal oxidizer 44.

The PSA process is of itself a well-known means of separating and purifying a less readily adsorbable gas component contained in a feed gas mixture of said component with a more readily adsorbable second component, considered as an impurity or otherwise. Adsorption commonly occurs in multiple beds of a solid adsorbent at an upper adsorption pressure, with the more selectively adsorbable second component thereafter being desorbed by pressure reduction to a lower desorption pressure. The beds may also be purged, at pressures above or below that of atmospheric pressure and typically at such lower pressure for further desorption and removal therefrom of said second component, i.e., the removal of impurities with respect to a high purity product gas, before repressurization of the beds to the upper adsorption pressure for the selective adsorption of said second component from additional quantities of the feed gas mixture as the processing sequence is carried out, on a cyclic basis, in each bed in the PSA system. Such PSA processing is disclosed in the Wagner, U.S. Pat. No. 3,430,418, and in the Fuderer et al., U.S. Pat. No. 3,986,849, wherein cycles based on the use of multi-bed systems are described in detail. Such cycles are commonly based on the release of void space gas from the product end of each bed, in so called cocurrent depressurization step(s), upon completion of the adsorption step, with the released gas typically being employed for pressure equalization and for purge gas purposes. The bed is thereafter countercurrently depressurized and/or purged to desorb the more selectively adsorbed component of the gas mixture from the adsorbent and to remove such gas from the feed end of the bed prior to the repressurization thereof to the adsorption pressure.

The PSA system can be operated with at least one, and typically at least two adsorbent beds, as may be desirable in the given applications, with from three to about 12 or more adsorbent beds commonly being employed in conventional practice.

While the PSA system produces a high-BTU fuel that can be sold directly to the pipeline or converted to CNG or LNG, the low-BTU tail gas produced by the PSA system is too low in heating value to be useful as a fuel and requires disposal in a flare or thermal oxidizer. This tail gas is, however, large in volume and represents a considerable loss of valuable methane. The present invention is a method for fully utilizing the otherwise wasted tail gas as a fuel supplement.

In the present invention, the low-quality tail gas stream from the PSA is utilized as a fuel, especially as a fuel for the boilers in the anaerobic digestion system. In one embodiment of the present invention, the low-quality tail gas stream from the PSA is blended with the higher quality gas from the anaerobic digester to produce a fuel suitable for burning in boilers designed to operate on lower quality gaseous fuel. In one embodiment, the method for utilizing the tail gas stream comprises: (1) compressing the biogas feed stream from the anaerobic digester; (2) sending a portion of the compressed biogas feed stream to be used as boiler fuel; (3) using a pressure swing adsorption (PSA) system that utilizes a vacuum pump on the compressed biogas feed stream to remove the carbon dioxide, moisture, hydrogen sulfide, and other contaminants as a tail gas; (4) mixing the tail gas with the portion of compressed biogas feed stream; (5) using an analyzer signal to measure the composition of the combined stream whereby the analyzer signal controls the amount of biogas stream to be mixed with the tail gas to ensure that the combined stream contains a high enough heating value that it can be used as a fuel; and (6) sending the mixed stream to the boilers to be used as fuel. In the above process, the PSA unit removes the bulk of the carbon dioxide from the methane product stream which reduces the carbon dioxide levels in the methane product stream to less than 5% carbon dioxide, or more particularly, less than 2% carbon dioxide. The tail gas of the PSA unit contains a low amount of methane, which is too low in heating value to be useful as a fuel. However, the tail gas is significantly large in volume that it represents a considerable loss of valuable methane. Thus, by blending the tail gas with a portion of the biogas feed, the tail gas can be fully utilized as a fuel.

Figure 2:
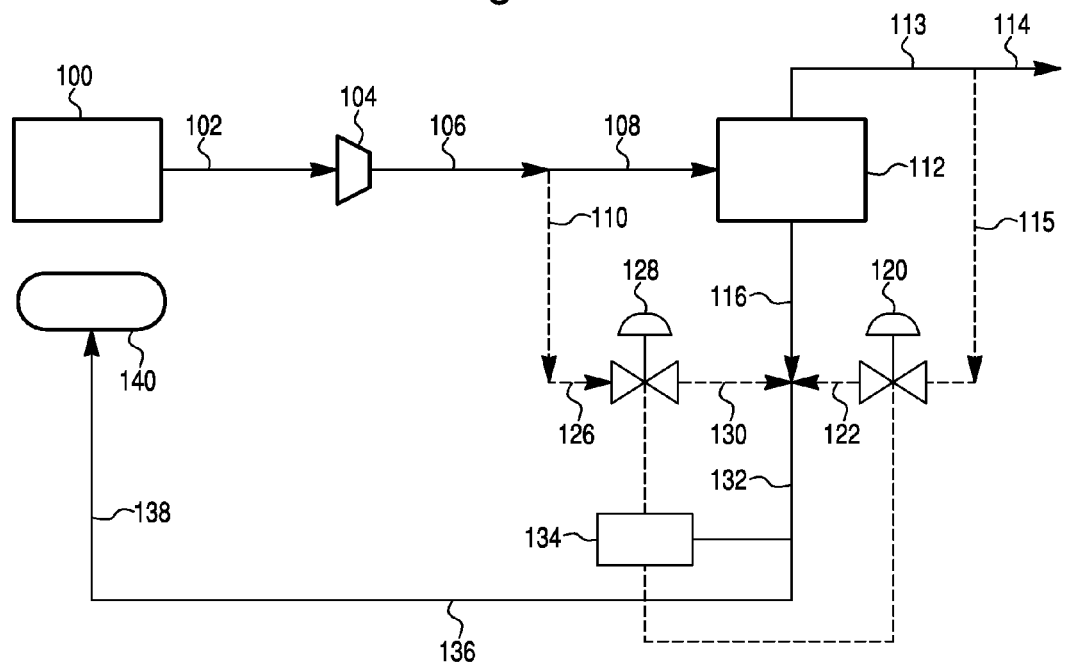
FIG. 2 represents a schematic of the process of embodiments of the present invention which illustrates a novel process for utilizing the tail gas from a pressure swing adsorption unit.

FIG. 2 illustrates an embodiment of the present invention. The biogas system is similar to the system displayed in FIG. 1 except that, in one embodiment, the tail gas from the PSA unit is mixed in with a portion of the biogas feed stream, and the resulting mixture is used as fuel. In practice, the PSA bed operation can be adjusted to compensate for changes in the feed composition and desired product purity.

One embodiment illustrated in FIG. 2 is an anaerobic digester 100 that produces a biogas feed stream 102. Again, anaerobic digester 100 can be any known unit used to convert a biomass to a biogas containing methane. The biogas feed stream 102 is directed from anaerobic digester 100 to a compressor 104. The biogas feed stream is compressed from about atmospheric to about 100 psig. The compressed stream 106 is divided into two streams whereby the majority of the biogas is sent as stream 108 to a pressure swing adsorption unit 112 and a portion of the biogas is sent as stream 110 to be mixed with the PSA tail gas as will be more fully described below. The compressed biogas stream 108 is fed to a PSA (with a vacuum pump) unit 112, which removes much of the carbon dioxide, moisture, hydrogen sulfide, and other contaminants from the biogas feed by means of a solid adsorbent. As discussed earlier, the adsorbent material used in the PSA unit 112 can be any known methane selective adsorbent material. Adsorbent materials suitable for use in the PSA unit 112 include, but are by no means limited to, activated carbon; carbon molecular sieve (CMS) adsorbents; activated alumina; silica gels; zeolites; and the titanium silicates. One skilled in the art is able to select a given adsorbent material or mixtures thereof, for use with a given feed gas mixture and desired product materials. A high purity methane output stream 113 is discharged at one end of the PSA unit 112. The PSA unit also delivers a low pressure output stream 116 containing the desorbed impurities from the adsorption beds, which is generally referred to as "tail gas". The composition of the tail gas stream 116 is enriched in carbon dioxide, moisture, hydrogen sulfide, and other contaminants relative to the permeate biogas feed stream 108. However, a significant reasonable amount of methane is also adsorbed and removed in the tail gas by the PSA unit 112. As discussed previously, the concentration of methane in the tail gas is not sufficient to produce a fuel stream. However, the volume of the tail gas is high such that methane loss from the PSA unit 112 in the tail gas may be significant. Accordingly, in one embodiment of the present invention, the tail gas stream 116 is blended with a portion of the biogas feed stream to produce a fuel suitable for burning in boilers. As described earlier, the compressed biogas feed stream 106 is divided whereby a portion of the biogas feed stream is sent as stream 110 to be mixed with the tail gas stream 116. The composition of the mixed gas stream 132 can be controlled by measuring the composition of in the mixed gas stream 132 by an analyzer signal 134. For example, the composition of the mixed gas stream 132 can be controlled whereby the carbon dioxide and/or the methane and/or the heating value in the mixed gas stream is measured by an analyzer signal 134 and depending on the carbon dioxide/methane/heating value level required to ensure complete combustion of the mixed gas stream 132, the analyzer signal 134 controls the amount of biogas feed to be mixed in with the tail gas stream 116 by controlling valve 128. The mixed gas stream 132 is then used as fuel for the boilers 140. By blending the low quality tail gas 116 with higher quality biogas feed stream 110, a fuel suitable for burning in boilers is produced. The ratio of the portion of biogas feed removed, stream 110, to the total biogas feed stream 106 is typically 10-60%, or more particularly, 15-50%, or more particularly, 20-35%. The combined gas stream 132 contains about 30-55% methane, or more particularly, 35-50% methane, or more particularly 40-50% methane.

Another embodiment of the present invention is illustrated in FIG. 2. Instead of dividing the compressed stream 106 into two streams as described in an earlier embodiment, the high purity methane output stream 113, which is discharged at one end of the PSA unit 112, is divided into two streams whereby the majority of the high purity methane output stream is sent as a product stream 114 and a portion of the high purity methane output stream is sent as stream 115 to be mixed with the PSA tail gas. The low pressure output stream ("tail gas") 116, which is delivered by the PSA unit 112 and contains the desorbed impurities from the adsorption beds, is blended with the portion of the high purity methane output stream 115 to produce a fuel suitable for burning in boilers. The composition of the mixed gas stream 132 can be controlled by measuring the composition of in the mixed gas stream 132 by an analyzer signal 134. For example, the composition of the mixed gas stream 132 can be controlled whereby the carbon dioxide and/or the methane and/or the heating value in the mixed gas stream is measured by an analyzer signal 134 and depending on the carbon dioxide/methane/heating value level required to ensure complete combustion of the mixed gas stream 132, the analyzer signal 134 controls the amount of high purity methane output stream to be mixed in with the tail gas stream 116 by controlling valve 120. The mixed gas stream 132 is then used as fuel for the boilers 140. By blending the low quality tail gas 116 with high quality methane gas stream 115, a fuel suitable for burning in boilers is produced. The ratio of the portion of product stream removed, stream 115, to the total product stream 113 is typically 10-60%, or more particularly, 15-50%, or more particularly, 20-35%. The combined gas stream 132 contains about 30-55% methane, or more particularly, 35-50% methane, or more particularly 40-50% methane.

Another embodiment of the present invention is illustrated in FIG. 2. Rather than dividing the compressed biogas feed stream 106 as described above or dividing the high purity methane output stream 114 also described above, the cycles of the PSA unit 112 are adjusted such that the tail gas 116 from the PSA unit 112 contains sufficient methane concentration, thus producing a fuel suitable for burning in boilers. In one embodiment of the present invention, the cycles of the PSA unit 112 are increased, which results in an increase in the amount of methane adsorbed by the PSA unit 112. With the increase in amount of methane adsorbed, the amount of methane in the tail gas increases. Thus, by adjusting the cycles of the PSA unit 112, a fuel suitable for burning in boilers is produced.

Figure 3:
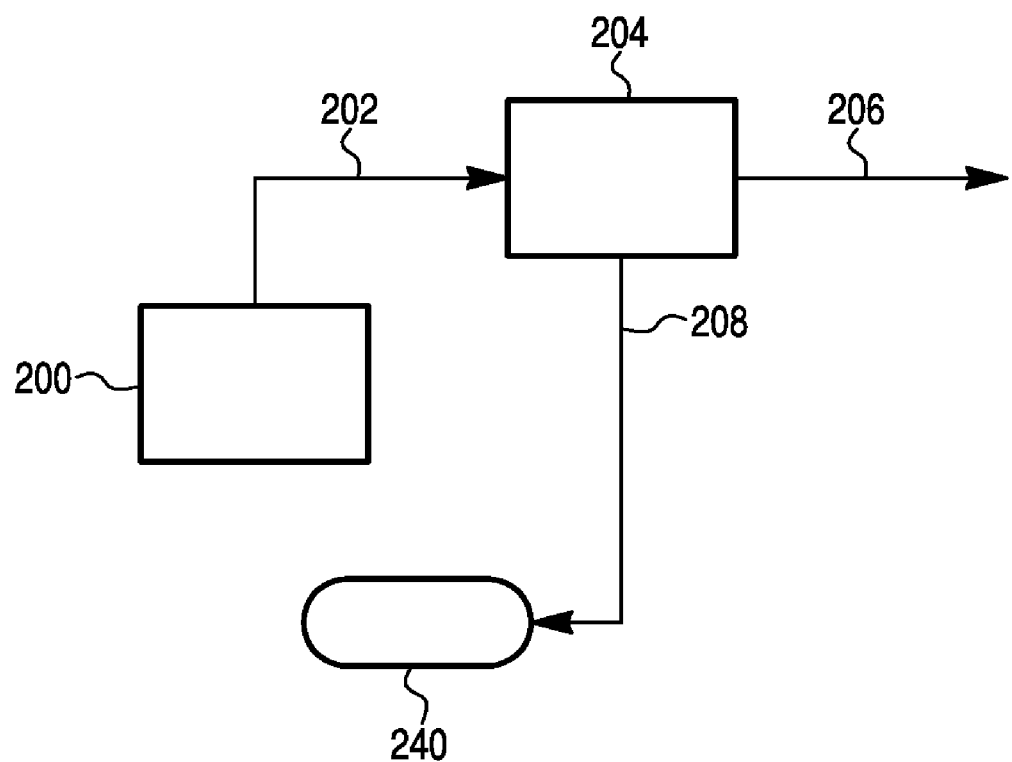
FIG. 3 represents a schematic of the process of an embodiment of the present invention which illustrates a novel process for utilizing the tail gas from a membrane separation unit.

Another embodiment of the present invention is illustrated in FIG. 3. An anaerobic digester 200 produces a biogas feed stream 202. Again, anaerobic digester 200 can be any known unit used to convert a biomass to a biogas containing methane. The biogas feed stream 202 is directed from anaerobic digester 200 to a membrane unit 204 where the bulk of the impurities, such as carbon dioxide, moisture, hydrogen sulfide, and other contaminants from the biogas feed, are removed via line 208 as permeate and enriched non-permeated methane product stream is produced as stream 206. Similar to a PSA separation system, a significant reasonable amount of methane is also retained in the permeate stream 208, but the concentration of methane in the permeate is not sufficient to produce a fuel stream. However, the volume of the permeate is high such that methane loss from the membrane unit 204 in the permeate may be significant. In an embodiment of the present invention, the membrane unit 204 is adjusted such that the permeate 208 from the membrane unit 204 contains sufficient methane concentration, thus producing a fuel suitable for burning in boilers.

A variety of types of suitable designs of membrane separation systems can be used depending upon the desired gas separation. The membrane may be employed in plate and frame form, or may comprise spiral wound film membranes, tubular membranes, hollow fiber membranes, or the like. The use of hollow fiber membranes is generally preferred due to the high surface area per unit of membrane that can be obtained thereby. It will be appreciated that, when membranes are used in tubular or hollow fiber form, a plurality of such membranes can conventionally be arranged in parallel bundle form. In such embodiments, the feed gas stream can be brought into contact with either the outer or shell side, or the inner or tube side of the membrane particles. Those skilled in the art will appreciate that the flow of the feed gas and of the permeating gas within the separation zone can be either cocurrent or countercurrent. Using bundles of hollow fiber and tubular membranes, the passage of feed gas can be either radial or axial with respect to the direction in which the hollow fibers or tubular membranes are positioned within the separation zone.

Typical of the types of membrane materials utilized in membrane separation processes include metallic and inorganic membranes as well as various organic polymeric materials or such organic polymeric materials mixed with inorganic materials such as fillers, reinforcements and the like. Organic polymers that may be considered for various practical commercial operations include such materials as polysulfones; polystyrenes, including such styrene-containing polymers as acrylonitrile, styrene copolymers, styrene-butadiene and styrene-vinylbenzyl halide copolymers; cellulosic polymers, such as cellulose acetate, cellulose acetate-butyrate, methyl or ethyl cellulose; polyamides and polyimides; polycarbonates; polyurethanes; polyesters, including polyacrylates, polyethylene; polypropylene; polyvinyl pyridines, and the like. Such polymers may be either substituted or unsubstituted, with typical substituents of such substituted polymers including halogens, such as chlorine, fluorine and bromine; hydroxyl groups; lower alkyl groups; monocyclic aryl; lower acyl groups, etc.

The use of a permeable membrane in conjunction with a coating material is also known, with such combinations enabling good selectivity of separation to be achieved together with high flux through the membrane. Typical coatings include substituted or unsubstituted polymers that are either solid or liquid under gas separation conditions. Examples of such coating materials include synthetic and natural rubbers, organic prepolymers, polyurethanes, polyamines, polyesters and the like. The coatings may be polymerized either before or after the application thereof to the permeable membrane with which they are to be employed. The above descriptions of membrane designs, types of materials and coatings are provided for illustrative purposes and form no significant part of the present invention.

EXAMPLE 1

The benefits of the invention can be seen in Tables 1 and 2. Table 1 shows various gas flows and usages at a typical wastewater treatment plant that utilizes an anaerobic digester to produce a biogas and a PSA system to upgrade the biogas produced according to the prior art FIG. 1 (without tail gas reuse). Table 2 shows various gas flows and usages at a typical wastewater treatment plant, which utilizes an anaerobic digester to produce a biogas and a PSA system to upgrade the biogas produced according to the present invention (with tail gas reuse).

TABLE 1

Representative Gas Flows from WWTP Anaerobic Digester with PSA Gas Recovery without Tail Gas Reuse

|  | Total Digester Biogas | Digester Gas as Process Boiler Fuel | PSA Feed | PSA Product | Tail Gas to Flare |
| --- | --- | --- | --- | --- | --- |
| Gas Flow, scfh | 30,000 | 15,000 | 15,000 | 8,954 | 6,046 |
| % Methane (dry basis) | 65 | 65 | 65 | 98 | 16 |
| Million BTU/hr | 19.5 | 9.75 | 9.75 | 8.8 | 0.95 |

TABLE 2

Representative Gas Flows from WWTP Anaerobic Digester with PSA Gas Recovery with Tail Gas Reuse

|  | Total Digester Biogas | Digester Gas Portion as Process Boiler Fuel | PSA Feed | PSA Product | Tail Gas Portion as Boiler Fuel | Total Gas as Boiler Fuel |
| --- | --- | --- | --- | --- | --- | --- |
| Gas Flow, scfh | 30,000 | 13,350 | 16,650 | 9,939 | 6,711 | 20,061 |
| % Methane (dry basis) | 65 | 65 | 65 | 98 | 16 | 48.7 |
| Million BTU/hr | 19.5 | 8.7 | 10.8 | 9.7 | 1.1 | 9.8 |

As can be seen in Table 1, the anaerobic digester produces about 30,000 scfh of biogas. Of the 30,000 scfh of biogas, 15,000 scfh is used to fuel the process boiler. The remaining 15,000 scfh of biogas is then sent to the PSA where the PSA purifies the biogas stream containing 65% methane to a high quality methane product stream containing 98% methane, which can be sold directly to the pipeline or converted to CNG or LNG. The process seen in Table 1 produces 8,954 scfh of high quality methane product, but also produces 6,046 scfh of low methane tail gas. The tail gas contains only 16% methane and cannot be used as a fuel for the process boilers, so the tail gas is disposed of in a flare or thermal oxidizer. However, because the volume of the tail gas is significantly large at 6,046 scfh, the disposal of the tail gas represents a loss of 0.95 million BTU/hr.

As can be seen in Table 2, by using the present invention where the tail gas produced by PSA system is mixed with the biogas produced by the anaerobic digester and the mixed stream is utilized as fuel for the boilers, the amount of biogas that is produced by the anaerobic digester sent and to the process boiler to be used as fuel is reduced to 13,350 scfh from 15,000 scfh in Table 1. Thus, more biogas is fed to the PSA system, which increases the volume of high quality methane product stream produced by the PSA system to 9,939 scfh compared to 8,954 scfh shown in Table 1. For boilers that can accommodate lower BTU fuels, in this example 48.7% methane, tail gas reuse in the present invention can increase the available sales gas by 10% or greater. Furthermore, significantly reducing or eliminating the use of the flare can substantially reduce the capital cost of the PSA system.

What is claimed is:

1. A process for producing a biogas comprising:
    (a) producing a biogas feed stream in an anaerobic digestion system;
    (b) compressing said biogas feed stream;
    (c) passing at least a portion of the compressed biogas feed stream to a separation unit, said separation unit discharging a purified, methane-containing product gas therefrom and a low-quality gas stream comprising a minor amount of methane, carbon dioxide and other impurities present in said biogas feed stream; and
    (d) either combining said low-quality gas stream with a portion of said biogas feed stream, or with a portion of said purified, methane-containing product gas for use as a fuel in said anaerobic digestion system.

2. The process of claim 1 wherein said separation unit is a pressure swing adsorption system discharging a purified, methane-containing product gas therefrom as a less readily adsorbable component of said biogas feed stream and discharging a low-quality gas stream as a tail gas containing more readily adsorbable components comprising a minor amount of methane, carbon dioxide and other impurities present in said biogas feed stream.

3. The process of claim 1 wherein said combining of said portion of said biogas feed stream with said low-quality gas stream to form a combined gas stream is controlled by analyzing the composition of the combined gas stream and controlling the portion size of the biogas feed stream mixed with said low-quality gas stream.

4. The process of claim 1 wherein the ratio of said portion of said biogas feed stream combined with said low-quality gas stream to said biogas feed stream from said anaerobic digestion system is 10-60%.

5. The process of claim 1 wherein the ratio of said portion of said biogas feed stream combined with said low-quality gas stream to said biogas feed stream from said anaerobic digestion system is 15-50%.

6. The process of claim 1 wherein the ratio of said portion of said biogas feed stream combined with said low-quality gas stream to said biogas feed stream from said anaerobic digestion system is 20-35%.

7. The process of claim 1 wherein either of the combined gas streams is utilized as a fuel for a boiler that provides heat for the anaerobic digestion system.

8. The process of claim 1 wherein either of the combined gas streams contains 30-55% methane.

9. The process of claim 1 wherein either of the combined gas streams contains 40-50% methane.

10. The process of claim 3 wherein the composition of said combined gas stream is analyzed by measuring the methane and/or carbon dioxide and/or the heating value of said combined gas stream.

11. The process of claim 1 wherein said combining of said portion of product gas with the low-quality gas is controlled by analyzing the methane and/or carbon dioxide and/or heating value of the combined stream and controlling the portion size of the product gas mixed with the low-quality gas stream.

12. The process of claim 1 wherein the ratio of said portion of said methane-containing product gas combined with said low-quality gas stream to said purified methane-containing product gas stream is 10-60%.

13. The process of claim 1 wherein the ratio of said portion of said methane-containing product gas combined with said low-quality gas stream to said purified methane-containing product gas stream is 15-50%.

14. The process of claim 1 wherein the ratio of said portion of said methane-containing product gas combined with said low-quality gas stream to said purified methane-containing product gas stream is 20-30%.

15. The process of claim 1 wherein said separation unit is a membrane system, said membrane system discharging as a non-permeate, said purified, methane-containing product gas therefrom and permeating a said low-quality gas stream.

* * * * *